United States Patent [19]

Feingold

[11] Patent Number: 4,871,351

[45] Date of Patent: Oct. 3, 1989

[54] IMPLANTABLE MEDICATION INFUSION SYSTEM

[76] Inventor: Vladimir Feingold, 49 Gumnut Road, Cherrybrook, New South Wales 2120, Australia

[21] Appl. No.: 89,957

[22] Filed: Aug. 26, 1987

Related U.S. Application Data

[63] Continuation of Ser. No. 775,593, Sep. 13, 1985, abandoned.

[30] Foreign Application Priority Data

Sep. 28, 1984 [AU] Australia .............................. PG7415

[51] Int. Cl.$^4$ .............................................. A61M 5/20
[52] U.S. Cl. ....................................... 604/66; 604/65; 604/93; 604/131; 128/Dig. 12
[58] Field of Search ............. 128/419 P, 419 PG, 903, 128/DIG. 1, DIG. 12; 604/50–53, 65, 66, 93, 95, 131, 132, 891, 140; 623/8

[56] References Cited

U.S. PATENT DOCUMENTS

| | | |
|---|---|---|
| 3,692,027 | 9/1972 | Ellenwood, Jr. ...................... 604/50 |
| 4,146,029 | 3/1979 | Ellinwood, Jr. ................. 128/419 P |
| 4,190,048 | 2/1980 | Sampson . |
| 4,253,201 | 3/1981 | Ross et al. ............................... 623/8 |
| 4,258,711 | 3/1981 | Tucker et al. ............... 128/DIG. 12 |
| 4,313,527 | 2/1983 | Fischell ........................ 128/DIG. 12 |
| 4,332,634 | 6/1982 | Aperavich ............................... 623/8 |
| 4,360,019 | 11/1982 | Portner et al. ....................... 604/131 |
| 4,395,259 | 7/1983 | Prestele et al. ............. 128/DIG. 13 |
| 4,403,984 | 9/1983 | Ash . |
| 4,447,224 | 5/1984 | DeCant, Jr. et al. ....... 128/DIG. 12 |
| 4,487,603 | 12/1984 | Harris . |
| 4,494,545 | 1/1985 | Slocum et al. .................. 128/419 P |
| 4,494,950 | 1/1985 | Fischell ............................... 128/903 |
| 4,496,343 | 1/1985 | Prosl et al. ........................... 604/131 |
| 4,511,355 | 4/1985 | Franetzki et al. ................... 604/131 |
| 4,515,584 | 5/1985 | Abe . |
| 4,525,165 | 6/1985 | Fischell ...................... 128/DIG. 12 |

FOREIGN PATENT DOCUMENTS

| | | |
|---|---|---|
| 39124 | of 0000 | European Pat. Off. . |
| 78636 | 5/1983 | European Pat. Off. .... 128/DIG. 12 |
| 3306115 | 8/1984 | Fed. Rep. of Germany ... 128/429 P |

OTHER PUBLICATIONS

Radioshack Dictionary of Electronics; Howard W. Sams & Co. 1978; pp. 126 and 495.
Peoples Home Health Care 1/85; p. 32.
"Microcomputer Controlled Devices for Human Inplantation" by R. E. Fischell, Johns Hopkins APL Technical Digest vol. 4 #2, 1983, pp. 96–103.

*Primary Examiner*—Francis Jaworski
*Assistant Examiner*—D. Shay
*Attorney, Agent, or Firm*—Ladas & Parry

[57] ABSTRACT

An implantable medication delivery system comprising an implantable unit with a refillable reservoir, a catheter connected thereto, and a pumping mechanism activated by a microcomputer or microprocessor for pumping medication from the reservoir through the catheter into the body. The implantable medication unit receives information and control commands via a telemetry link from an external controller unit having a microprocessor. The external controller receives feedback in the form of intermittent sampling of blood using enzyme strips and a reflectance meter and/or additional sensor(s) which measure(s) physiological parameter(s) such as heart rate or blood pressure or temperature or skin resistivity. The feedback information is processed by the external unit in accordance with a mathematical model of the patient and the relevant parameters are transmitted to the implanted unit which adjusts its delivery profile according to a prescribed algorithm. The external unit can also detect an alarm condition and take appropriate steps, e.g. abort infusion.

8 Claims, 6 Drawing Sheets

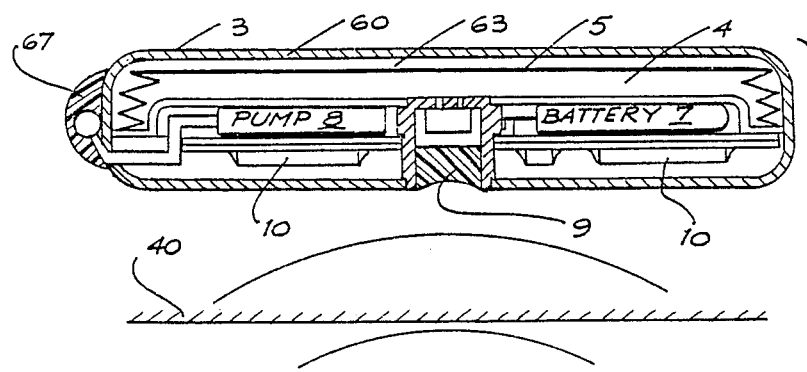
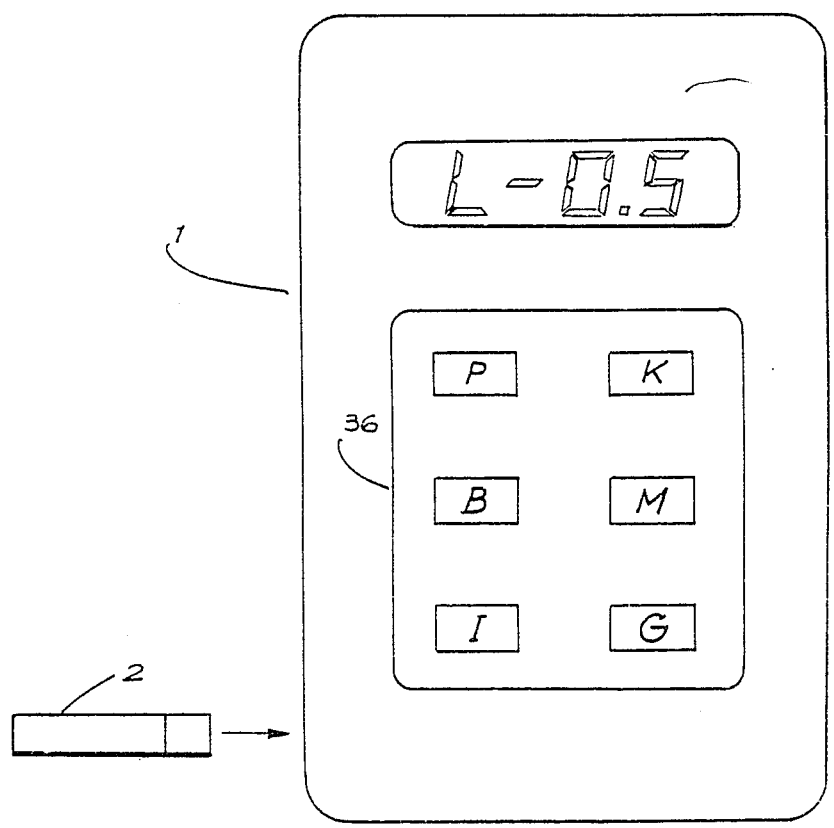
FIG. 1

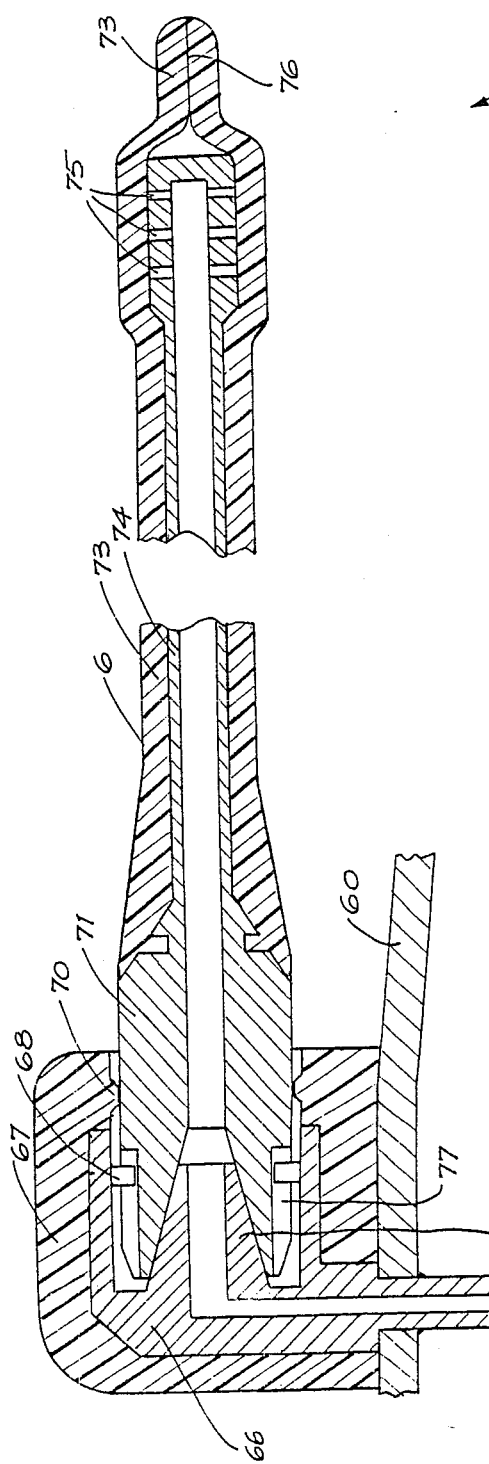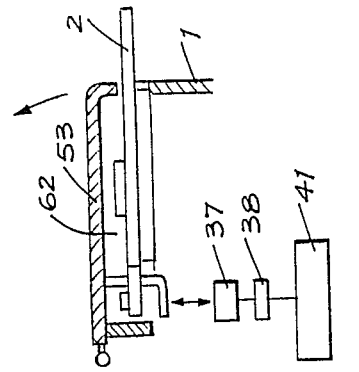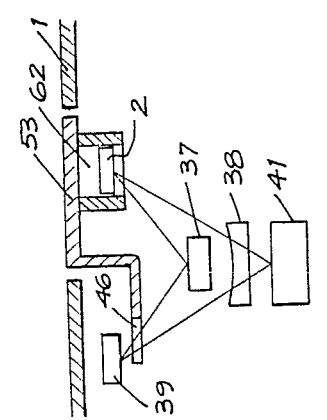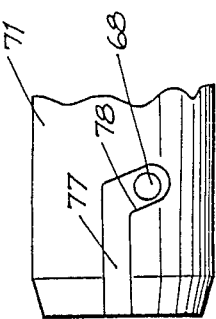

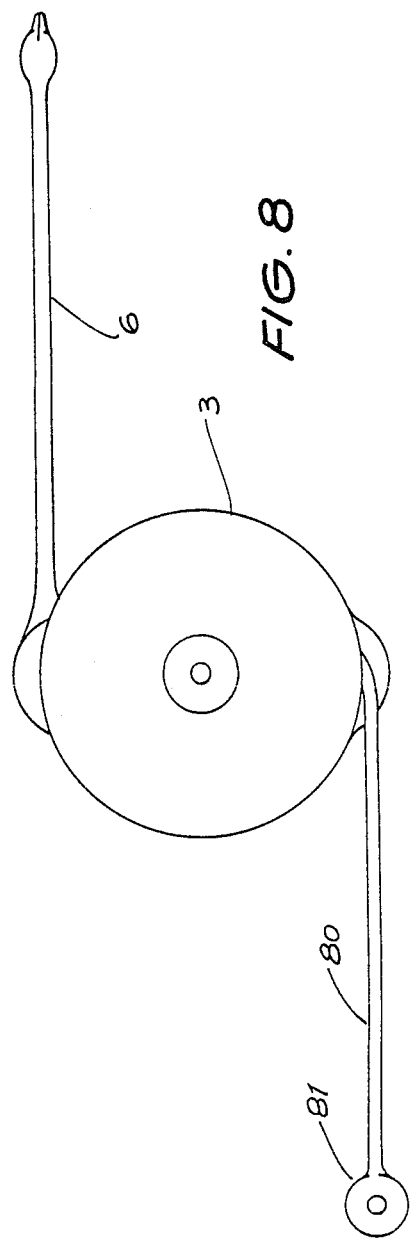
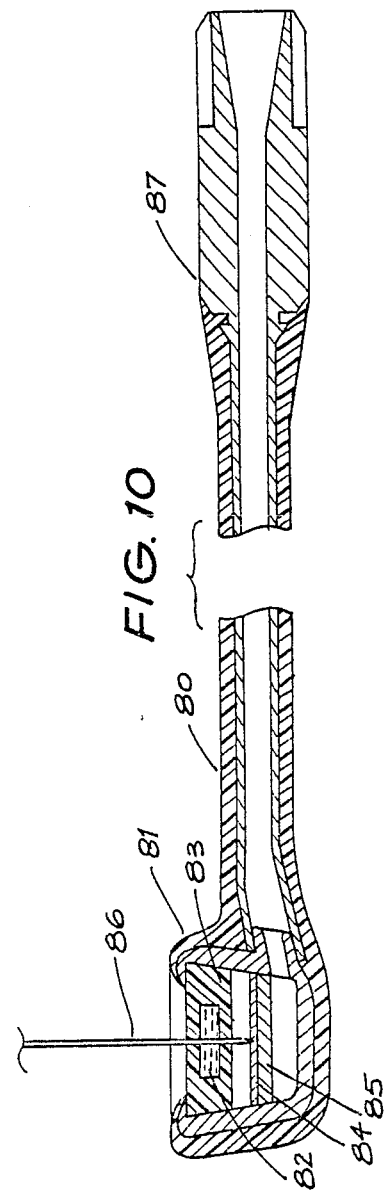

IMPLANTABLE MEDICATION INFUSION SYSTEM

This is a continuation of co-pending application Ser. No. 775,593 filed on Sept. 13, 1985 now abandoned.

The present invention relates to an open loop implantable medication infusion system with a feedback control option. In a preferred embodiment, the invention is directed to an implantable insulin delivery system for diabetics, although the invention is not limited thereto.

Certain human disorders, such as diabetes, require the injection into the body of prescribed amounts of medication at prescribed times or in response to particular conditions or events. Various kinds of infusion pumps have been propounded for infusing drugs or other chemicals or solutions into the body at continuous rates or measured dosages. Examples of such known infusion pumps and dispensing devices are found in U.S. Pat. Nos 3,731,861; 3,692,027; 3,923,060; 4,003,379; 3,951,147; 4,193,397; 4,221,219 and 4,258,711. Some of the known pumps are external and inject the drugs or other medication into the body via a catheter, but the preferred pumps are those which are fully implantable in the human body.

Implantable pumps have been used in infusion systems such as those disclosed in U.S. Pat. Nos. 4,077,405; 4,282,872; 4,270,532; 4,360,019 and 4,373,527. Such infusion systems are of the open loop type. That is, the systems are pre-programmed to deliver a desired rate of infusion. The rate of infusion may be programmed to vary with time and the particular patient. A major disadvantage of such open loop systems is that they are not responsive to the current condition of the patient, i.e. they do not have feedback information. Thus, an infusion system of the open loop type may continue dispensing medication according to its pre-programmed rate or profile when, in fact, it may not be needed.

There are known closed loop infusion systems which are designed to control a particular condition of the body, e.g. the blood glucose concentration. Such systems use feedback control continuously, i.e. the patient's blood is withdrawn via an intravenous catheter and analysed continuously and a computer output signal is derived from the actual blood glucose concentration to drive a pump which infuses insulin at a rate corresponding to the signal. The known closed loop systems suffer from several disadvantages. First, since they monitor the blood glucose concentration continuously they are complex and relatively bulky systems external to the patient, and restrict the movement of the patient. Such systems are suitable only for hospital bedside applications for short periods of time and require highly trained operating staff. Further, some of the known closed loop systems do not allow for manually input overriding commands. Examples of closed loop systems are found in U.S. Pat. Nos. 4,055,175; 4,151,845 and 4,245,634.

An implanted closed loop system with some degree of external control is disclosed in U.S. Pat. No 4,146,029. In that system, a sensor (either implanted or external) is arranged on the body to sense some kind of physiological, chemical, electrical or other condition at a particular site and produced data which corresponds to the sensed condition at the sensed site. This data is fed directly to an implanted microprocessor controlled medication dispensing device. A predetermined amount of medication is dispensed in response to the sensed condition according to a pre-programmed algorithm in the microprocessor control unit. An extra-corporeal coding pulse transmitter is provided for selecting between different algorithms in the microprocessor control unit. The system of U.S. Pat. No. 4,146,029 is suitable for use in treating only certain ailments such as cardiac conditions. It is unsuitable as a blood glucose control system for example, since (i) it is not practicable to measure the blood glucose concentration continuously with an implanted sensor and (ii) the known system is incapable of dispensing discrete doses of insulin in response to certain events, such as meals and exercise. Furthermore, there are several disadvantages to internal sensors; namely, due to drift, lack of regular calibration and limited life, internal sensors do not have high long-term reliability. If an external sensor is used with the system of US Patent No. 4,146,029, the output of the sensor must be fed through the patient's skin to the implanted mechanism. There are inherent disadvantages to such a system, namely the high risk of infection. Since the algorithms which control the rate of infusion are programmed into the implanted unit, it is not possible to upgrade these algorithms without surgery. The extra-corporeal controller merely selects a particular one of several medication programs but cannot actually alter a program.

It is an object of the present invention to overcome, or substantially ameliorate the above described disadvantages of the prior art by providing an implantable open loop medication infusion system with a feedback control option.

Accordingly, in its broadest form, the present invention provides an implantable medication infusion system comprising an implantable unit for controllably dispensing medication into the body; an external controller adapted to communicate with said implantable device when implanted via a telemetry link, and sensor means for sensing a condition of the body such as temperature, heart rate, skin resistivity or blood glucose level, the output of said sensor being connected to said external controller.

It is to be noted that in the present invention, the output of the sensor means is fed to the external controller. The sensed data is processed in the external controller which then transmits appropriate signals to the implanted device to infuse the appropriate dosage.

Typically, the implanted unit infuses medication in accordance with a preselected profile which can be determined from the patient's history, i.e. the system normally functions as an open loop system. However, at intermittent times, the condition of the patient can be sensed and fed to the external controller which, in turn, overrides the predetermined profile to vary the dosage as required.

The external controller is programmed to adapt to the particular patient by monitoring the sensed conditions of the patient in response to different times and dosages of medication. Thus, by suitable programming, the system is self-learning and adaptive. Further, from past performance of the particular patient, the system can suggest the times at which further readings should be taken after a particular dosage is given so as to give a true and faithful indication of the actual condition of the patient.

The program in the external controller can be updated without the requirement of surgery. Moreover, the sensor can be checked and calibrated to ensure that it is oprating properly.

In a preferred embodiment, the implantable medication delivery system comprises an implantable unit with a refillable reservoir, a catheter connected thereto, and a pumping mechanism activated by a microcomputer or microprocessor for pumping medication from the reservoir through the catheter into the body. The implantable medication unit receives information and control commands via a telemetry link from an external controller unit having a microprocessor. The external controller receives feedback in the form of intermittent sampling of blood using enzyme strips and a reflectance meter and/or additional sensor(s) which measure(s) physiological parameter(s) such as heart rate or blood pressure or temperature or skin resistivity. The feedback information is processed by the external unit in accordance with a mathematical model of the patient and the relevant parameters are transmitted to the implanted unit which adjusts its delivery profile according to a prescribed algorithm. The external unit can also detect an alarm condition and take appropriate steps, e.g. abort infusion.

Notwithstanding other forms of the invention, preferred embodiments thereof will now be described with reference to the drawings in which:

FIG. 1 is a schematic view of the system of the preferred embodiment;

FIGS. 6A is a schematic front cross sectional view of the gating arrangement of the reflectance meter of FIGS. 2 and 3;

FIG. 6B is a schematic side cross sectional view of the gating arrangement of the reflectance meter of FIGS. 2 and 3;

FIG. 7A is a cross sectional view of a catheter suitable for use with the implanted unit of FIG. 2.

FIG. 7B is a plan view of the end of the catheter of FIG. 7A;

FIG. 8 is a schematic plan view of a reservoir flushing system suitable for use with the implanted unit of FIG. 1;

FIG. 10 is a cross-sectional view of a catheter of the flushing system of FIG. 8.

Figure 2:
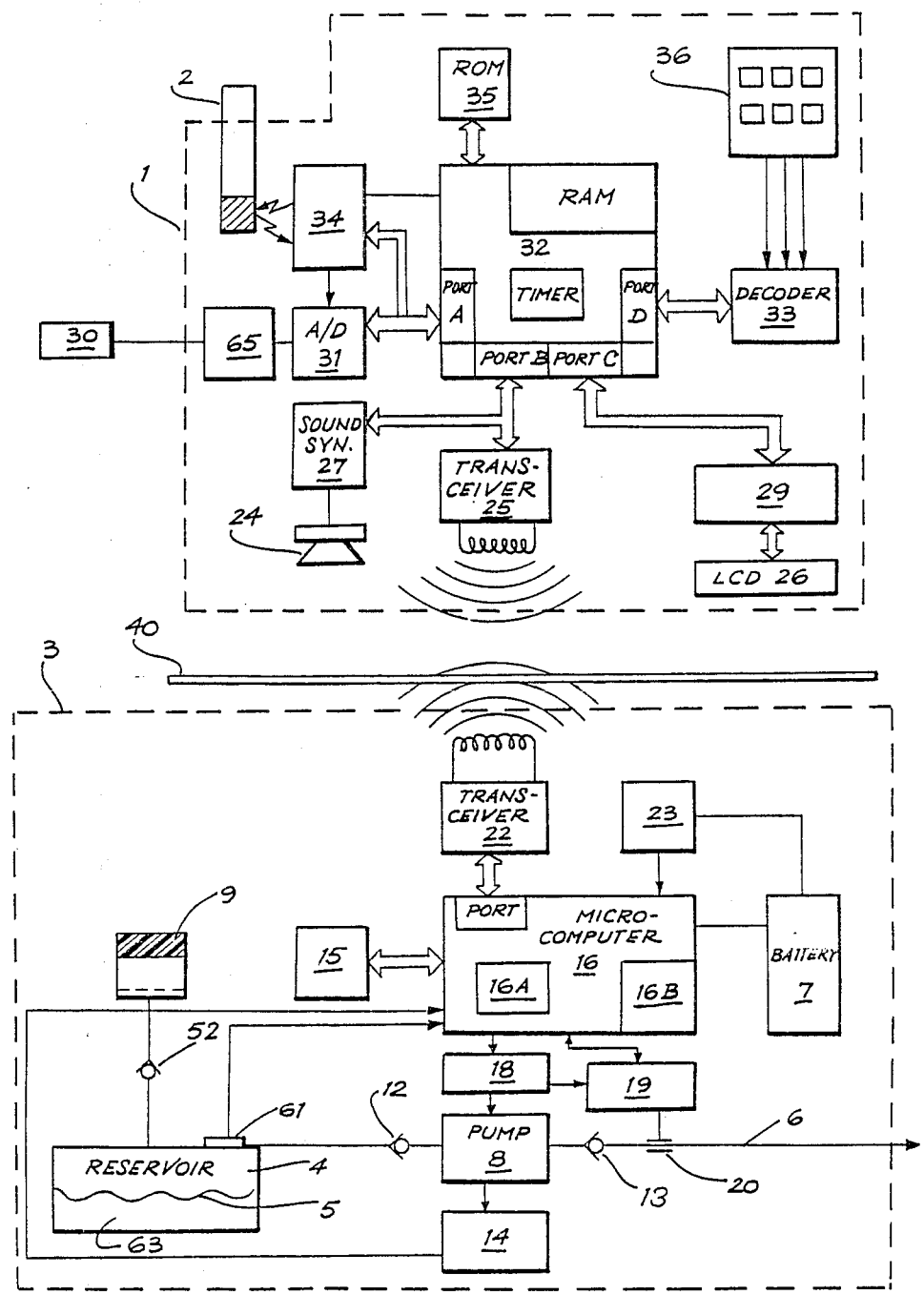
FIG. 2 is a block diagram of the system of FIG. 1.

The implantable medication system of the preferred embodiment comprises the following major sub-systems shown in FIG. 1; an external controller 1, an enzyme test strip 2 for use in determining the blood glucose concentration and an implantable unit 3. It may also comprise a sensor 30 (FIG. 2) for sensing physiological conditions such as heart rate and blood pressure, temperature, skin resistivity or any other relevant body condition.

The implantable unit 3 comprises a reservoir 4 separated by a diaphragm 5 from a liquid/vapour chamber 63 saturated with freon 113 which maintains the reservoir at a pressure equilibrium less than atmospheric pressure, provided that the system is kept at body temperature. Freon 113 has a linear pressure characteristic from −4 psig (at 90° F.) to approximately −2.5 psig (at 104° F.). Using freon 113, the medication reservoir 4 will be maintained at a pressure below that of the human body pressure up to altitudes of 8,500 ft. For patients who may live above that altitude, other fluorocarbons at lower pressure may be employed. In this way, should there be a leak from the reservoir, the effect would be to cause body fluids to diffuse slowly into the reservoir 4 rather than to have a rapid flow of medication enter into the body where it could harm the patient. Because of the pressure differential between the body and the medication reservoir 4 the medication will not flow from the reservoir 4 into the body. As the amount of medication in the reservoir 4 varies, the flexible diaphragm 5 moves up or down, with the freon 113 being converted either from liquid to vapour or vapour to liquid to provide an essentially constant pressure which will always be below one atmosphere and below normal body pressure.

Figure 4:
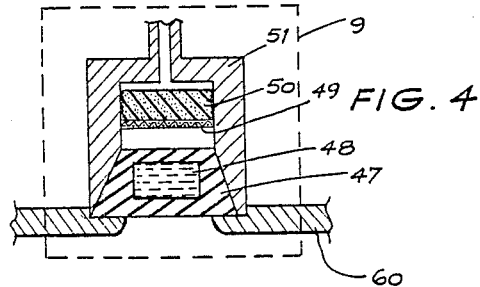
FIG. 4 is a schematic cross sectional view of the refilling port of FIG. 2.

The reservoir 4 can be refilled percutaneously with a syringe. As shown in FIG. 4, a self-sealing refilling port 9 is provided for this purpose. The refilling port 9 is made out of an elastomer 47 such as silicon rubber surrounding a gel sealant 48. The fluid is injected by the syringe (not shown) which pierces the elastomer 47 and the gel 48. The holes left by the syringe in the elastomer 47 will be filled by the high viscosity gel 48. Thus, the refilling port may be used many times over. The tip of the syringe is stopped by a metallic strainer 49 which in addition prevents any solid debris from entering the reservoir 4. The injected fluid then passes through a filter in the form of a porous foam plug 50 in order to prevent any large air bubbles and fibril aggregates entering the system.

Typically, the reservoir 4 and syringe have inner surfaces of medication compatible material e.g. hydrophilic material.

The entry to the reservoir 4 is also protected by a check valve 52 (FIG. 2) for preventing leaks back into or out from the refilling port 9, and another check valve 12 for preventing similar leaks from a pumping mechanism 8 which pumps the medication from the reservoir 4 through a catheter 6 into a desired site in the body.

The implantable unit 3 is powered by a lithium battery 7 and the pumping parameters are controlled and monitored by an electronics circuit 10. The above elements are hermitically sealed within a titanium case 60 to protect them from any adverse effects by body fluids. The controller unit 1 is kept outside the patient body. The function of the external controller unit 1 is to calculate the required medication infusion regimen and serve as a communication link between the patient/physician and the implantable delivery unit 3. Furthermore, it serves to close the loop by sampling the blood glucose level through glucose test strips 2, or sensor 30 which may monitor blood pressure, heart rate or act as a needle type glucose sensor which can be inserted subcutaneously.

Figure 5:
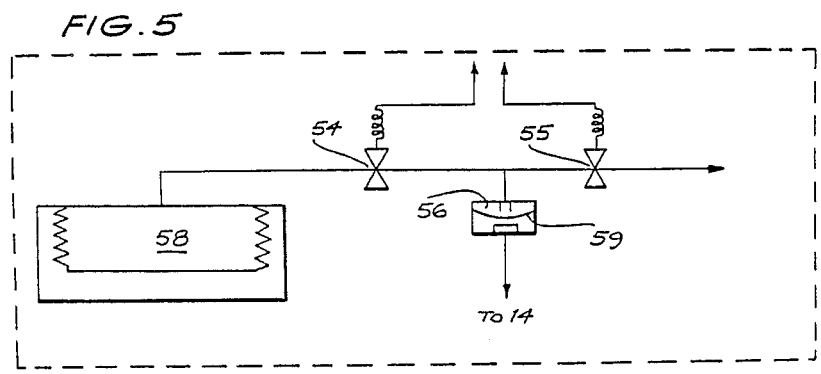
FIG. 5 is a schematic diagram of another embodiment of a pumping mechanism suitable for use with the implanted unit of FIG. 2.

FIG. 2 illustrates the mechanical and electrical arrangements of the system in block diagrams. The medication fluid is refilled through the self-sealing port 9 into the reservoir 4 which is connected to the pumping mechanism, such as a solenoid activated reciprocating piston. The pumping mechanism 8 has inlet and outlet check valves 12, 13 to minimize back-flow. Typically, each stroke of the reciprocating piston will displace a volume of 0.1 microlitre of medication fluid. Any known suitable pump, such as those described in the prior art patents referred to above, can be used. An alternative pumping mechanism is shown in FIG. 5. In this arrangement, the reservoir chamber 58 is arranged as disclosed in U.S. Pat. No. 3,731,681 where the reservoir 58 is maintained above arterial pressure. The pumping is achieved by opening an inlet solenoid valve 54 which allows the fluid to flow into chamber 56 as the pressure in this chamber ($P_2$) is less than the pressure ($P_1$) of reservoir 58. Valve 54 is then shut and solenoid valve 55 is opened to enable the fluid in the chamber 56 to be displaced by a resilient flexible membrane 59 which had been subject to pressure $P_1$ and now returns to its resting position. To complete the cycle and prepare the mechanism for the next pumping cycle, the valve 55 is shut off. In this pumping system, the pressure at the outlet $P_3$ must be less than $P_2$ which in turn must be less than $P_1$. The valves 54 and 55 can be controlled by the microprocessor 16 via suitable drivers. It is to be noted that in the pumping arrangement of FIG. 5, no positively acting pump is required, and power requirements of the implanted unit are therefore reduced.

The rate of infusion is controlled by a microprocessor or microprocessor 16 which is part of the implantable unit 3. Throughout the specification, the term "microcomputer" is intended to mean any miniature electronic computing device, e.g. a microprocessor. Within the memory 15 of the microcomputer, there is stored a program which determines the pattern of pulsing of the pumping mechanism 8 over a period of time, as described hereafter. The microcomputer 16 drives the pump 8 via a driver 18. The microcomputer 16 has a built-in timer 16A which maintains continuously the time of day in a variable location inside a random access memory 16B of the microcomputer. Through radio frequency telemetry and transceivers 22, 25, the external controller unit 1 transmits a set of infusion rate points to the implantable unit which will store them in the RAM 16B. Consequently, the microcomputer 16 of the implantable unit will execute a new profile determined by the transmitted information. During the execution of the delivery rate, various safety factors are monitored. For example, the state of the reservoir is checked using transducer 61 which will be activated once the reservoir reaches 15% of its capacity. The pumping performance of the solenoid pump 8 is monitored by circuit 14 which analyzes the shape of the voltage applied to the solenoid pump 8. Any irregularities in the shape such as voltage level or timing to the pulse peak are flagged to the microcomputer 16. Further, if the pumping rate is exceeded, a maximum rate monitor in the circuit 14 shuts off the microcomputer 16. Any lack of flow, or excessive flow, is checked by circuit 19 which is connected to a transducer 20 attached to the wall of a flexible tube at the output of the pump 8 prior to exit from the implantable unit 3. Typically, the transducer 20 is a piezoceramic plate, strain gauge or pick-up needle device which converts minor displacements to electrical signals.

The condition of the battery 7 is checked by a low voltage detector 23, and if a predetermined low level is reached, the state is flanged to the microcomputer 16. Low battery level can be indicated either if the battery 7 reaches maximum impedance value or mininum operational voltage. Once either of these states are detected, it is immediately transmitted to the external unit 1 to warn the patient that the service life of the battery has been reached and removal of the implantable medication unit is required within an acceptable time frame.

The value of the patient's blood glucose concentration is obtained by placing a sample drop of blood on a glucose test strip 2 and inserting the test strip into a reflectance meter 34. The glucose reading is converted into a digital value by analog-to-digital convertor 31 and passed to a part of a microcomputer 32 in the external controller 1. The value can be displayed on a display, such as a liquid crystal display 26 driven by LCD driver 29, for the patient to check.

Figure 3:
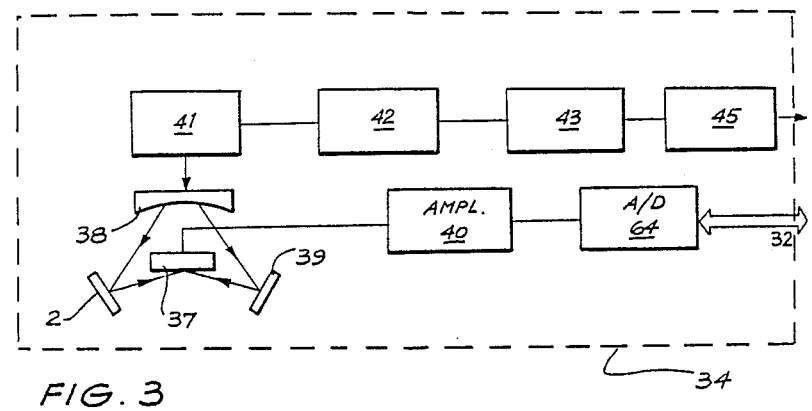
FIG. 3 is a schematic block diagram of the reflectance meter of FIG. 2.

A preferred construction of the reflectance meter 34 is shown schematically in FIG. 3. Light is emitted by a light emitting diode 41 and the light beam is then split by beamsplitter 38 into two beams; one beam is reflected onto a reference colour strip 39 and the other beam is reflected onto the test strip 2. Both beams are then reflected onto a photodetector diode 37. The intensity of the colour of the strip is related to the level of blood glucose. Typically, a strip impregnated in peroxidase, 3.3 dimethyl 4.4 diaminobiphenyl dihydrochloride and 2.7 diaminofluorene dihydrochloride is used. Referring to FIG. 6, when lid 53 of the reflectance meter is open and there is no test strip 2, the only source of light which falls upon the photodetector 37 is from the reference colour strip 39. Once a test strip is placed in the chamber 62 and the cover 53 is closed, shutter 46 blocks the light path from the reference colour strip 39 and the only source of light comes from the reflectance of the test strip 2. The reflectance meter includes a battery 43, power regulator 42 and battery tester 45.

By comparing the test strip colour to the reference colour, the colour intensity of the test strip 2 is determined and can be expressed in terms of glucose level. Preferably, the reference colour strip 39 is chosen to represent a colour corresponding to the middle of the blood glucose range. The current which is generated by the photodetector diode 37 is amplified by operational amplifier 40 and fed to an analog-to-digital converter 64 which in turn provides the information in digital form to the microcomputer 32. Preferably, a program in the microcomputer memory checks the level to ensure that it is not nonsensical on the basis of past information. If it is, the controller will request repeated measurement.

Other body conditions, such as heart rate, temperature, etc. can be monitored by a further sensor 30 the output of which is fed to the microcomputer 32 after signal condition in circuit 65 and digital conversion A/D converter 31.

On the basis of a mathematical model, a relationship between insulin and glucose level is established for the patient, e.g. by his physician. The parameters for this relationship have been previously identified during an insulin challenge testing pulse. From the latest blood glucose concentration reading and the mathematical model, a new infusion profile is determined for the next time period. In addition, the controller unit 1 will recommend the time at which the next blood glucose concentration should be measured in order to optimise the input information based on the mathematical model.

A keypad 36 is provided to enter data and infusion parameters for the intial setup. It can also be used to provide commands by the patient for meal delivery requirements or in the event that the system is run as an open loop system without blood glucose readings being used as feedback.

The communication between the implantable unit 3 and the external controller unit 1 is in digital mode using ASCII characters. Each character of information has a parity bit and the communication is done in full duplex in order to reduce the effect of noise and eliminate errors. The transmitted data is divided into nine windows of 500 microseconds. The first window is a standby window followed by 7 windows of ASCII code and an eighth window which is the parity bit. Zeroes and ones are represented by the phase shifts of 16 kHz bursts (phase shift modulation). Once a character is transmitted and the parity bit is verified, the receiving unit echoes the character back to unit which then compares the transmitted character with the received version. If the two match, transmission will continue, otherwise the transmitted character will be repeated. In the event that the system is exposed to an unusual source of interference and after a predetermined number of attempts to transmit the information have failed, the unit will abort transmission and a message will be displayed to that effect. The above method provides secure transmission. In the event that the transmitted character or information is nonsensical, no action will be taken by the implanted unit. This further reduces the risk of inadvertent programming.

The catheter 6 from the pump 8 to the body is shown in more detail in FIG. 7. The proximal end 71 of the catheter is connected to a tubing feedthrough 66 by pulling it from a tapered fitting 69. The locking is achieved by a bayonet type attachment in which pin 68 engages an "L" shaped slot 77 on the proximal end 71. In the connection procedure, the "L" shaped slot 77 is aligned with pins 68 and then pushed towards the tapered fitting 69. The proximal end 71 is rotated clockwise and pins 68 are engaged at the blind end of the slot and pushed by the slot wall 78 in such a manner as to provide further force in the direction of the tapered fitting, thereby locking the proximal end 71 onto the taper fitting 69. To disengage, the reverse procedure is adopted. In order to provide further rigidity and seal the connection, a top cover 67, typically constructed from an elastomer such as silicon rubber, is provided. The top of the transmitting cover 67 has a sealing ring or lip 70 which is compressed against the proximal end 71.

The body of the catheter is constructed from two concentric tubings. The inner tubing 74 is made from the same material as the proximal end 71, and preferably should by hydrophillic in order to make it compatible with the medication, typically insulin. The inner tube 74 has a very thin wall in order to provide flexibility. The outer tubing 73 is made from an elastomer such as silicon rubber, or a polyurethane which is compatible with blood as has been shown in pacemaker applications. The inner lumen of tubing 74 is blindly terminated. However, holes 75 are drilled on the side walls to provide outlet flow to the injected medication solution. The distal end is covered by the tubing 73 which is stretched over the side holes. At the outlet termination the tubing walls are collapsed at the interface 76 as a result of the inner body pressure ($P_0$) such as the arterial or venous blood pressure when there is no pumping occurring. However, when pumping takes place the pressure inside the catheter $P_1$ is greater than $P_0$ and the fluid flows through the side holes 75 and between the distal end and the stretched tubing 73 to open the interface 76 and exit into the blood stream. Once the pumping stops, the pressure inside the catheter drops below $P_0$ and the tubing walls collapse again, closing the interface and preventing any blood cells flowing into the inside of the catheter.

The implantable medication infusion system of the preferred embodiment can be operated in two modes; open loop or closed loop (with feedback). In the closed loop (feedback) mode, the external controller 1 accepts the feedback information from the sensor 30 or the glucose strip 2 and provides the necessary operational commands to the implantable unit 3 by telemetry. In this mode, there are two operational arrangements, in the first operational arrangement the external controller acts as a master and the implantable unit 3 operates in slave mode. The external controller unit 1 directly activates the pumping mechanism 8 via the telemetry link 22 - 25. In this instance all the infusion profiles and timing based on the mathematical model are calculated and executed by the external controller unit 1, while the principal purpose of the microcomputer 16 inside the implanable unit 3 is to provide a monitoring function of the implantable unit such as the state of the reservoir 4, condition of the battery 7 and flow characteristics. This information is periodically transmitted back to the external controller unit 1 which alerts the patient or physician of the state of the implantable unit. (A sound synthesizer 27 and speaker 24 are included in the controller for providing an audible alarm signal). In the second operational arrangement, the external controller 1 transmits via the telemetry link 22-25 only the infusion parameters to the microcomputer 16 inside the implanted unit 3. In this case, the microcomputer 16 calculates and determines the pulsing sequence for the pumping mechanism 8 which corresponds to the desired infusion pattern. It will be apparent to those skilled in the art that in the first arrangement, most of the intelligence and computing power is maintained in the external controller 1, while in the second arrangement more intelligence is programmed and made available to the implantable unit 3. It is worthwhile noting that the first arrangement is the preferred method since the software and algorithms in the external controller 1 can be updated from time to time to reflect new scientific and medical findings without the need to explant the implanted unit 3.

In the open loop mode, the external controller acts as a programmer to change the state of the implanted unit 3 in the range of selected infusion states such as continuous basal delivery and meal delivery profile in the case of a diabetic patient. In this mode, the patient or physician programs the implantable unit 3 to the new desired state using the external controller 1. Thereafter, the external controller 1 can be removed and the implantable unit 3 will continually and independently operate in the new state. The only time this state will be altered is when the patient uses the external controller 1 to program a new state. This second mode of operation has been used successfully in pacemaker applications.

It should be noted that during the first mode of operation (feedback control), the patient can be informed instantaneously of the condition of the implanted unit 3 by the external controller 1. However, in the second mode (open loop), the patient could only be alerted during the programming session. The closed loop feedback mode of operation is preferred in such instances as insulin delivery in a diabetic patient, but the open loop mode is adequate in such cases since the patient usually programs the implantable unit a few times a day during meal intake, during which an opportunity is provided to become informed of the internal state of the implanted unit.

A syringe is used with the above system to refill the reservoir. Preferably, the syringe and reservoir 4 are made from, or coated with, a hydrophilic material such as a polyamide e.g. nylon 6 or cellulose buterate. It has been found that such a syringe is more compatible with the medication e.g. insulin and other drugs, and less susceptible to aggregation.

Figure 9:
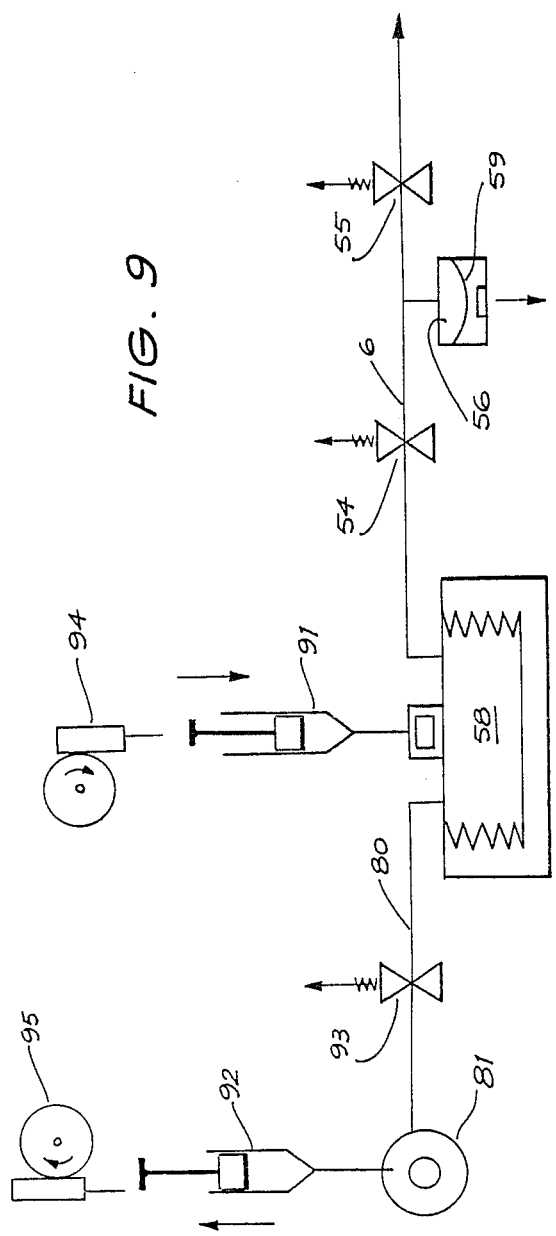
FIG. 9 is a schematic diagram of the hydraulics of the flushing system of FIG. 8.

According to another embodiment of the present invention, a flushing system is provided for the implantable unit 3. The flushing system is illustrated in FIGS. 8-10. As shown in FIG. 8, in addition to the normal catheter 6 used to dispense medication from the implantable unit 3, another catheter 80 is connected to the reservoir 4 (not shown) in the implantable unit 3. The catheter 80 is shown in more detail in FIG. 10. The body of the catheter 80 and its connecting end 87 are the same as the body and connecting end of the catheter 6. A filling port 81 is provided at the distal end of the catheter 80. The filling port 81 has a similar construction to the port 9 of the implantable unit 3, and comprises a gel sealant 82 surrounded by an elastomer 83 such as silicon rubber. The high viscosity gel 82 seals any holes left by the syringe 86 and enables the filling port to be used many times over. The tip of the syringe 86 is stopped by a metallic strainer 84. The injected fluid then passes through a filter, such as a porous foam plug 85, before entering the body of the catheter 80.

Operation of the flushing system will be described with reference to FIG. 9, which utilises the pumping system of FIG. 5. The valves 54, 55 are closed, and valve 93 is opened. Using a syringe 91, or alternatively an electric pump 94, fluid is pumped into the reservoir 58 under pressure. The fluid flows through the catheter 80 to the port 81 from where it is extracted by syringe 92 or alternatively an electric pump 95. In this manner, the reservoir 58 of the implanted unit 3 can be cleaned out by flushing. It is apparent that the direction of flushing may be reversed i.e. fluid can be inserted into port 81 and extracted from the reservoir 58. Furthermore, by opening valves 54, 55 and 93, fluid can be introduced into the body via port 81 and catheters 80 and 6. This arrangement allows manual input of medication.

The foregoing describes only some embodiments of the present invention, and modifications which are obvious to those skilled in the art may be made thereto without departing from the scope of the invention.

What is claimed is:

1. A medical infusion system intermittently switchable at selected times between an open loop system without feedback and a closed loop system with feedback, said system comprising an implantable unit including means for controllably dispensing medication into a body, an external controller, and an extra-corporeal sensor; wherein said implantable unit comprises an implantable transceiver means for communicating with a similar external transceiver means in said external controller to provide a telemetry link between said controller and said implantable unit, a first reservoir means for holding medication liquid, a liquid dispensing device, a pump connected between said reservoir means and said liquid dispensing device, and a first electronic control circuit means connected to said implantable transceiver means and to said pump to operate said pump; wherein said external controller comprises a second electronic control circuit means connected with said external transceiver means, a transducer means for reading said sensor, said transducer means having an output connected to said second electronic control circuit means, and a manually operable electric input device connected to said second electronic control circuit means; wherein said pump is operable by said first electronic control circuit means to pump said medication liquid from said first reservoir means to said liquid-dispensing device at a first predetermined rate independent of the output of said extra-corporeal sensor, and wherein said input device or said transducer means include means which selectively operable at intermittent times to respectively convey commands or output of said transducer representing the reading of said sensor to said second control circuit to instruct said first control circuit via said telemetry link to modify the operation of said pump.

2. A system as claimed in claim 1 wherein said first reservoir means contains liquid insulin and wherein said sensor comprises a blood glucose level indicator strip.

3. A system as claimed in claim 2 wherein said transducer means comprises a reflectance meter and an optical comparator to compare light reflected from said strip with light reflected from a reference strip internal of said transducer.

4. A system as claimed in claim 1 wherein said liquid dispensing device comprises a second reservoir means having a volume defined by a resilient diaphragm; a first liquid path connecting said first and second reservoir means; a first valve in said first liquid path; a second liquid path extending from said second reservoir means into a tissue system common with said implantable unit; and a second valve in said second liquid path; said first and second valves being connected to said first control circuit means and together with said resilient diaphragm constituting said pump whereby alternate sequential opening and closing of said first and second valves transfers medications liquid in said first reservoir means into said second reservoir means and then into the body.

5. A system as claimed in claim 1, further comprising a first refilling port connected to said first reservoir means, whereby said first reservoir means can be filled percutaneously through said first refilling port, said first refilling port comprising a volume having two opposite sides, one of said sides comprising a gel sealant surrounded by an elastomer through which a syringe needle may pass, and the other, opposite side comprising a syringe needle barrier member through which liquid may pass to said first reservoir means, a filter being located between said syringe needle barrier and said first reservoir means.

6. A system as claimed in claim 5 wherein said implantable unit includes a second filling port connected to said first reservoir means, and a valve connected between said second refilling port and said first reservoir means constituting a means for allowing a first syringe needle to be passed through the first refilling port, a second syringe needle to be passed through said second refilling port, and with said valve open liquid to be passed in either direction between said syringe needles to flush said first reservoir.

7. A system as claimed in claim 1, further comprising a catheter connected to said liquid dispensing device, said catheter comprising an inner conduit compatible with medication liquid contained in said first reservoir, and an outer conduit made from blood-compatible material.

8. A system as claimed in claim 7, wherein a proximal end of the catheter has a bayonet fitting for coupling to said liquid dispensing device; the inner conduit is terminated at a distal end of the catheter with at least one outlet therein, and the outer conduit extends beyond the inner conduit and is collapsed closed under normal internal body pressures, whereby in use fluid exits from said distal end of the catheter only when fluid pressure inside the catheter exceeds internal body pressure.

* * * * *